US008118807B2

(12) United States Patent
Thiagalingam et al.

(10) Patent No.: US 8,118,807 B2
(45) Date of Patent: Feb. 21, 2012

(54) BIOMEDICAL RETURN ELECTRODE HAVING THERMOCHROMIC LAYER

(75) Inventors: Aravinda Thiagalingam, Birchgrove (AU); Pramesh Kovoor, Wentworthville (AU); David Leslie Ross, Cheltenham (AU); Michael Anthony Barry, Werrington (AU)

(73) Assignee: Sydney West Area Health Service, New South Wales (AU)

( * ) Notice: Subject to any disclaimer, the term of this patent is extended or adjusted under 35 U.S.C. 154(b) by 1130 days.

(21) Appl. No.: 11/578,454

(22) PCT Filed: Apr. 18, 2005

(86) PCT No.: PCT/AU2005/000550
§ 371 (c)(1),
(2), (4) Date: Aug. 16, 2007

(87) PCT Pub. No.: WO2005/099606
PCT Pub. Date: Oct. 27, 2005

(65) Prior Publication Data
US 2008/0195089 A1 Aug. 14, 2008

(30) Foreign Application Priority Data

Apr. 16, 2004 (AU) .............................. 2004902049

(51) Int. Cl.
*A61B 18/16* (2006.01)
(52) U.S. Cl. .............................. 606/32; 606/35; 600/385
(58) Field of Classification Search .............. 606/32–35; 600/382–385, 372, 395
See application file for complete search history.

(56) References Cited

U.S. PATENT DOCUMENTS

| 3,998,215 A | * | 12/1976 | Anderson et al. ............. 600/397 |
| 4,303,073 A | | 12/1981 | Archibald |
| 4,416,277 A | | 11/1983 | Newton et al. |
| 4,494,541 A | | 1/1985 | Archibald |

(Continued)

FOREIGN PATENT DOCUMENTS

CA 2280313 2/2001

(Continued)

OTHER PUBLICATIONS

European Examiner's Report, Jan. 18, 2010, European Patent Office.

(Continued)

*Primary Examiner* — Linda Dvorak
*Assistant Examiner* — Amanda Scott
(74) *Attorney, Agent, or Firm* — Medlen & Carroll, LLP

(57) ABSTRACT

A biomedical return electrode for electrosurgery or radiofrequency (RF), a biomedical electrode pad (100), a system (300), and a method of treating tissue using a biomedical return electrode are disclosed. The biomedical return electrode comprises an electrode conductor (114) for receiving electrical energy from tissue via a return path, and a thermochromic liquid crystal (TLC) layer (116) coupled to the conductor (114). The TLC layer (116) changes color at one or more sites dependent upon the conductor temperature at each site. The TLC layer (116) changes color in a predetermined range of temperatures from about 40° C. to about 50° C. to alert an operator about the risk of a burn occurring. The biomedical electrode pad (100) comprises at least one such biomedical return electrode and a conductive body (112) to form a contact with tissue. The system (300) comprises an apparatus for delivering electrical energy to tissue and such a biomedical electrode pad (100). The system (300) may optionally comprise a color sensor (340) for viewing the pad (100) and monitoring equipment for remotely observing the pad (100).

90 Claims, 10 Drawing Sheets

U.S. PATENT DOCUMENTS

| | | | |
|---|---|---|---|
| 4,649,923 A | | 3/1987 | Hoffman |
| 4,763,659 A | * | 8/1988 | Dunseath, Jr. ................ 600/391 |
| 4,848,335 A | | 7/1989 | Manes |
| 5,058,999 A | * | 10/1991 | Davis ............................ 349/197 |
| 5,124,819 A | | 6/1992 | Davis |
| 5,817,091 A | | 10/1998 | Nardella |
| 5,902,272 A | * | 5/1999 | Eggers et al. ................ 604/114 |
| 6,063,075 A | | 5/2000 | Mihori |
| 6,174,309 B1 | | 1/2001 | Wrublewski et al. .......... 606/45 |
| 6,258,085 B1 | | 7/2001 | Eggleston |
| 6,466,299 B1 | * | 10/2002 | Lehtiniemi et al. ........... 349/199 |
| 2003/0036747 A1 | | 2/2003 | Ie et al. .............................. 606/1 |
| 2003/0114877 A1 | | 6/2003 | Gellman ....................... 606/192 |
| 2003/0216732 A1 | | 11/2003 | Truckai et al. .................. 606/49 |
| 2003/0220637 A1 | | 11/2003 | Truckai et al. .................. 606/28 |
| 2004/0044341 A1 | | 3/2004 | Truckai et al. .................. 606/41 |
| 2004/0186469 A1 | * | 9/2004 | Woloszko et al. .............. 606/41 |

FOREIGN PATENT DOCUMENTS

| | | |
|---|---|---|
| EP | 1596705 A1 | 11/2005 |
| WO | WO 03/005895 | 1/2003 |

OTHER PUBLICATIONS

Written Opinion of the international Searching Authority, May 24, 2005, PCT.

International Search Report, May 24, 2005, PCT.

M. Parsley, "The use of thermochromic liquid crystals in research applications, thermal mapping and non-destructive testing", pp. 53-58. This paper appears in: Semiconductor Thermal Measurement and Management Symposium, 1991. SEMI-THERM VII. Proceedings, Seventh Annual IEEE, Issue Date: Feb. 12-14, 1991.

Steinke et al., "Dispersive pad site burns with modern radiofrequency ablation equipment", *Surgical Laparoscopy, Endoscopy and Precutaneous Techniques*, vol. 13, Issue 6, pp. 366-371.

* cited by examiner

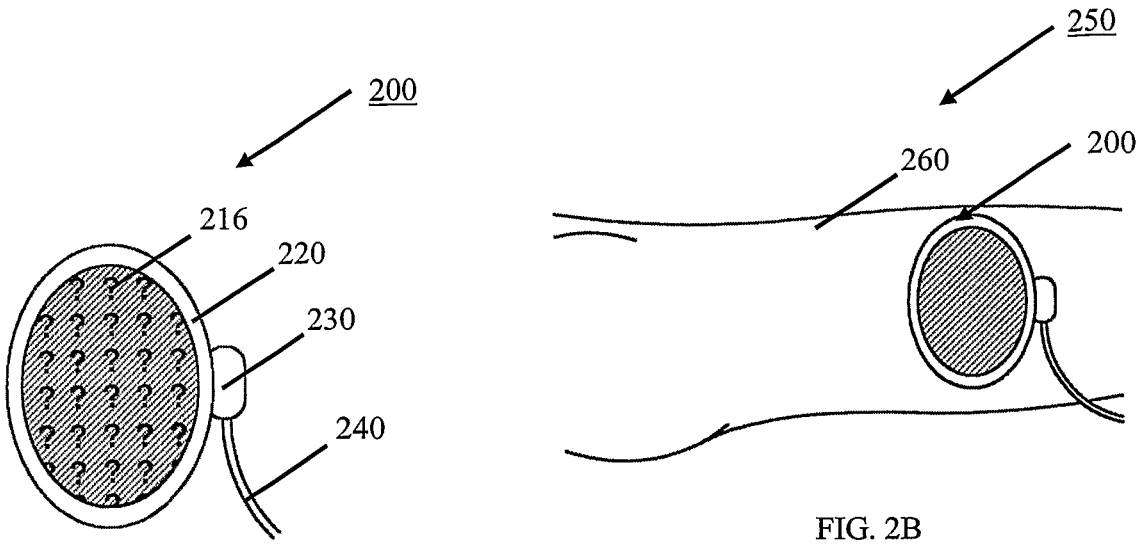
FIG. 2A
FIG. 2B
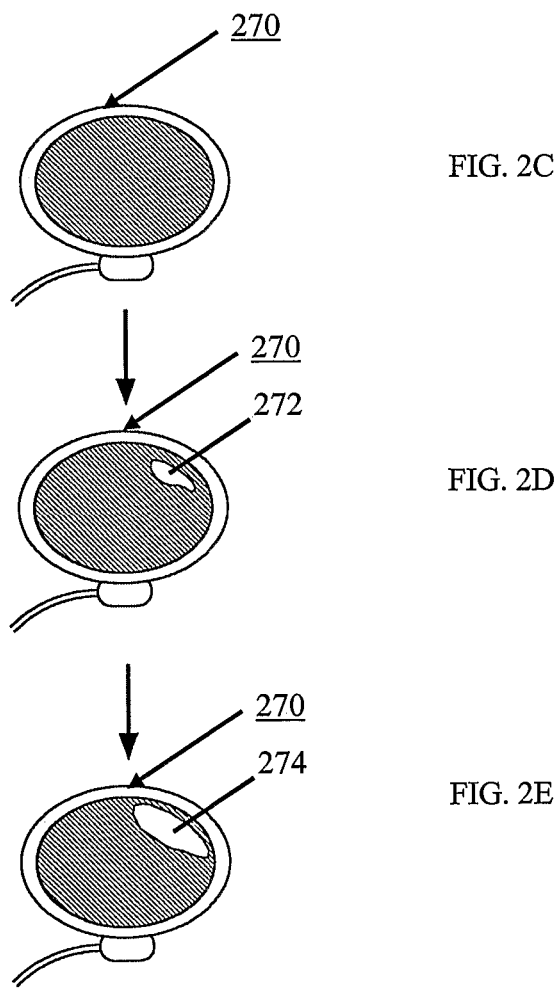
FIG. 2C
FIG. 2D
FIG. 2E

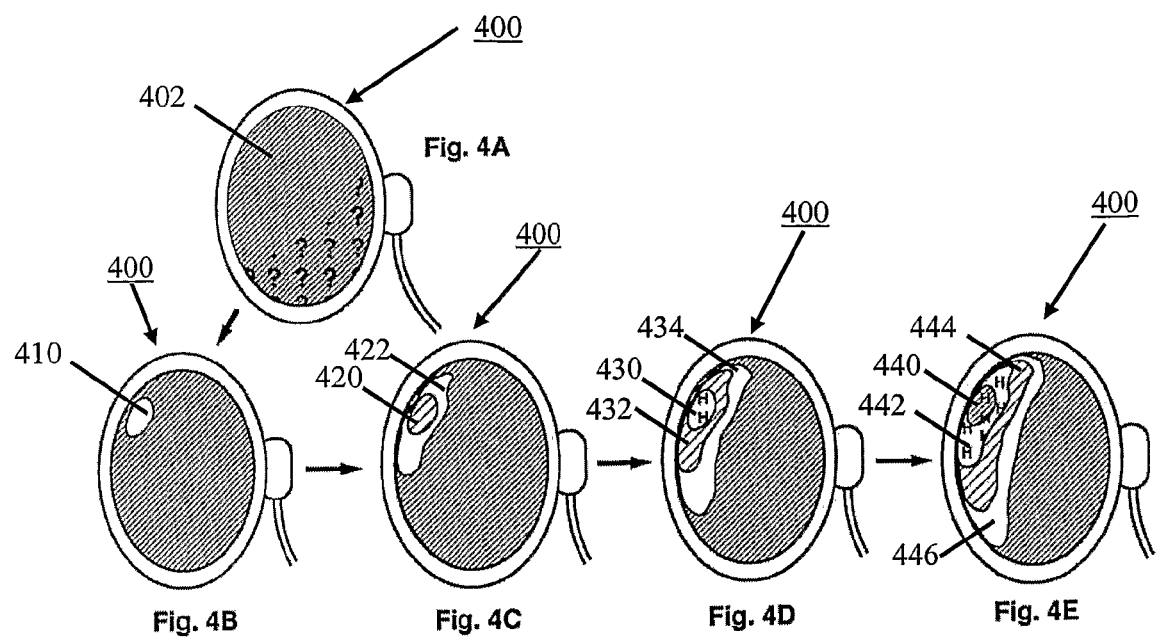
Fig. 4A
Fig. 4B
Fig. 4C
Fig. 4D
Fig. 4E
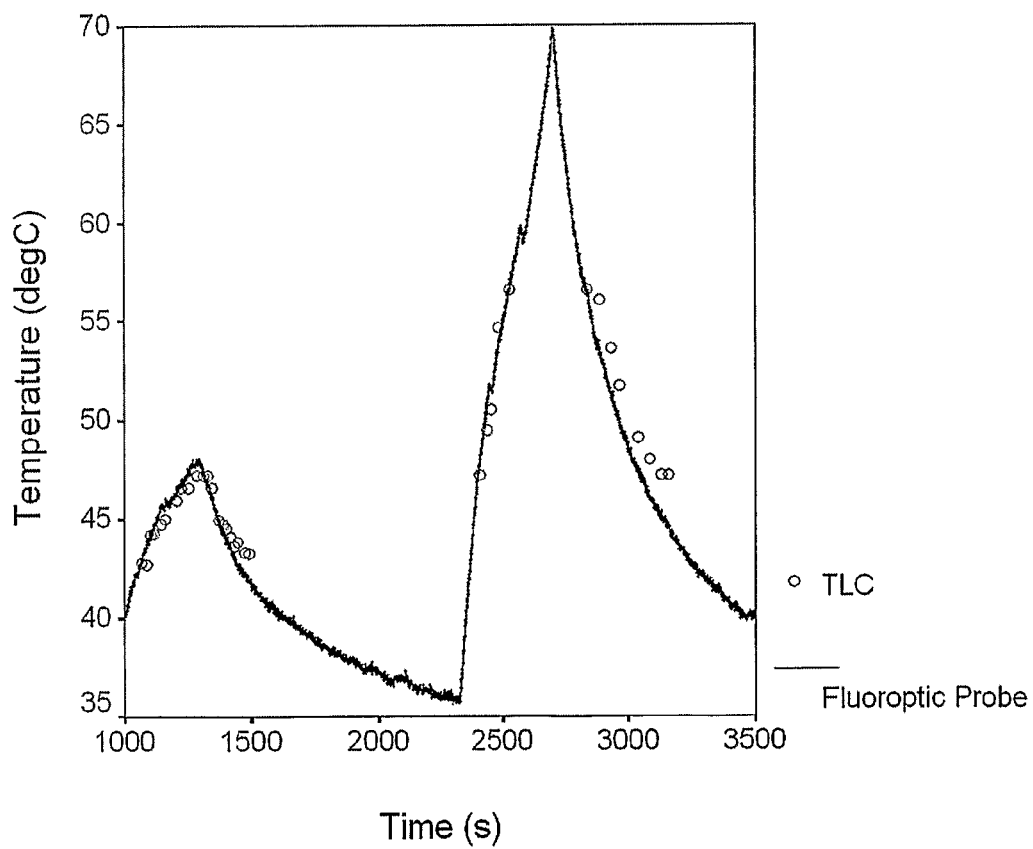
FIG. 9

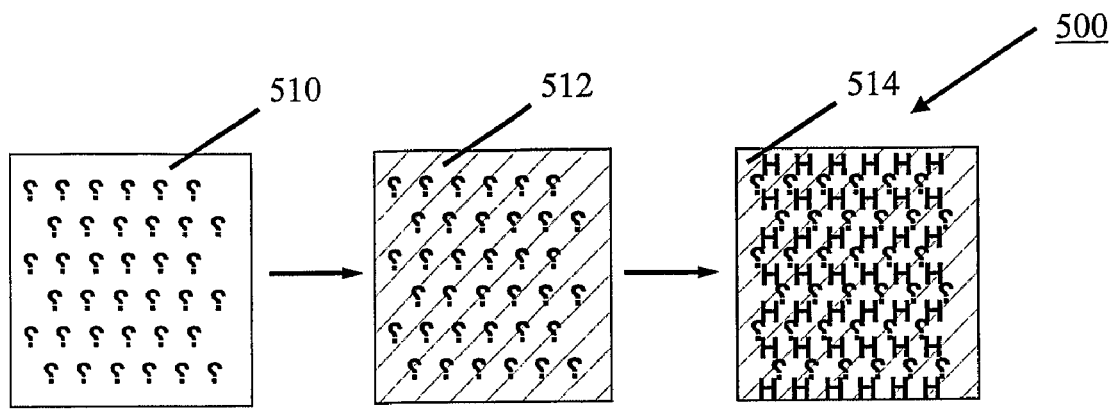
FIG. 5
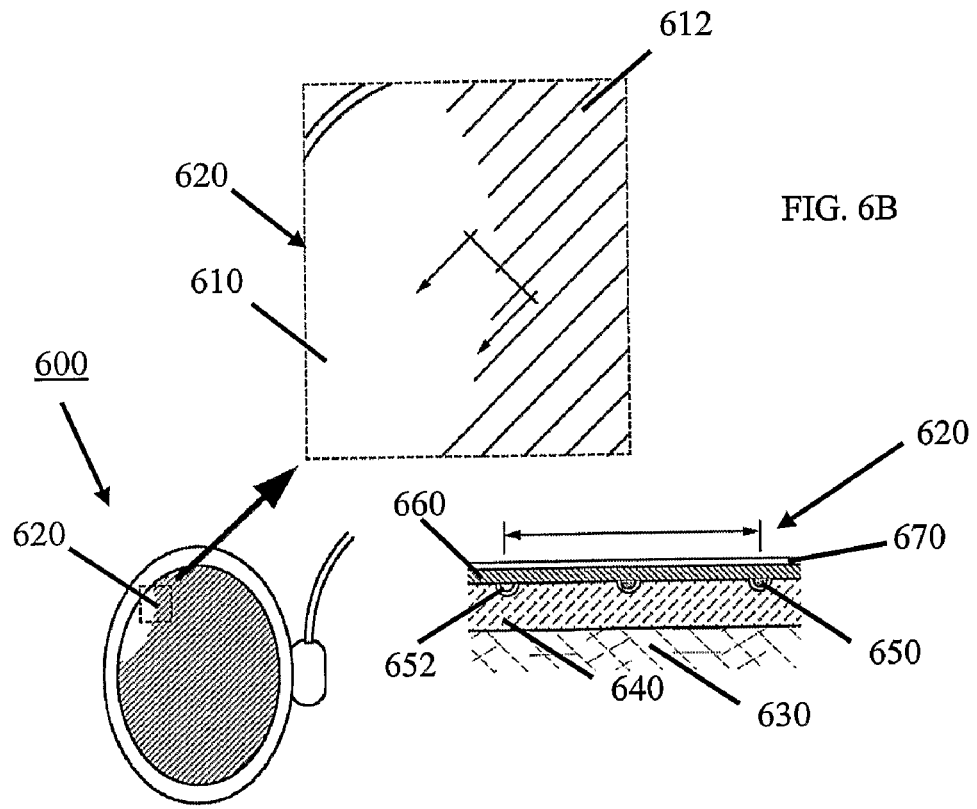
FIG. 6A
FIG. 6B
FIG. 6C

BIOMEDICAL RETURN ELECTRODE HAVING THERMOCHROMIC LAYER

This application is a U.S. national entry of International Application No. PCT/AU2005/000550, filed on Apr. 18, 2005, which claims priority to Australian Application No. 2004902049, filed on Apr. 16, 2004.

FIELD OF THE INVENTION

The present invention relates generally to surgical equipment and procedures and in particular to biomedical electrodes.

BACKGROUND

A number of surgical procedures utilise electrosurgical or radiofrequency (RF) ablation techniques. Electrical current is usually delivered through a surgical instrument, or catheter, to the tissue requiring treatment. The return path of the electrical current is generally directed back through a large dispersive electrode. Burns associated with excessive heating at such a dispersive electrode complicate 0.1%-4% of procedures utilising RF ablation and can cause serious morbidity.

Monitoring the temperature of the ablation electrode improves the safety of the ablation procedure and can usually be achieved by inserting a single temperature sensor at the tip of the catheter. The need for improved temperature monitoring at the dispersive electrode has been increasingly recognised recently, for example, Canadian Patent No. 2,280,313 in the name of Vilos (1998) and Steinke et al 'Dispersive pad site burns with modern radiofrequency ablation equipment' (see Surgical Laparoscopy, Endoscopy and Percutaneous Techniques Volume 13 Issue 6 Pages 366-71). However, monitoring the temperature of the dispersive electrode is considerably more difficult due to its large size. Dispersive electrode burns are frequently caused in circumstances where most of the dispersive electrode is not in contact with the patient, which results in a high current flow in the remaining section of the electrode in contact with the patient. In an attempt to detect this situation, numerous (>20) temperature monitoring devices may have to be positioned throughout the dispersive electrode. However, measuring temperatures at so many points using conventional sensors, such as thermocouples or thermistors, is cumbersome and makes the dispersive electrode costly.

Because of the difficulty of measuring temperature at the dispersive electrode, several systems have been proposed attempting to detect partial failure of the dispersive electrode by monitoring the impedance during ablation. Systems that measure the impedance (e.g., U.S. Pat. No. 6,063,075 issued to Mihori on 16 May 2000, U.S. Pat. No. 4,848,335 issued to Manes on 18 Jul. 1989, and U.S. Pat. No. 4,494,541 issued to Archibald in 22 Jan. 1985) or the voltage and current (e.g., U.S. Pat. No. 5,817,091 issued to Nardella et al. on 6 Oct. 1998) fail to address all cases, because a dispersive electrode that has partially detached from the patient has a small surface area, but may still have good contact in the remaining, attached area, and hence a low impedance. This situation produces a high RF current density in the attached area, and hence has the potential to cause burns to the patient.

Some systems have been designed that attempt to measure the adequacy of dispersive electrode contact with the patient by monitoring the capacitance at the patient electrode (e.g. U.S. Pat. No. 4,303,073 issued to Archibald on 1 Dec. 1981) or measuring the impedance between two separate portions of the dispersive electrode (e.g., U.S. Pat. No. 4,416,277 issued to Newton et al. on 22 Nov. 1983). U.S. Pat. No. 6,258,085 issued to Eggleston on 10 Jul. 2001 discloses a system that monitors the impedance at two separate portions of the dispersive electrode and the quantity of thermal energy delivered to the patient, and calculates the probable amount of cooling at the return electrode to derive the probability of a patient burn. These systems have the disadvantage that they do not detect partial removal of the dispersive electrode if both parts of the return electrode are reduced to the same size (i.e. the pad dislodges parallel rather than perpendicular to its long axis). The temperature that is achieved at the dispersive electrode is determined by many factors that cannot be assessed accurately in all cases such as the local tissue perfusion, or degree of subcutaneous fat and fibrous tissue. Hence, a system that attempts to estimate the temperature exposes the patient to a higher risk than a system that directly measures the temperature. These systems also require their own specialised electrosurgical current generators and hence cannot be used in cases where another type of electrosurgical current generator is required (e.g., where a specialised radiofrequency current generator capable of measuring temperatures at multiple thermocouples is required to deliver current to a specialised cardiological catheter). However, cases have been reported of burns being produced despite the use of these devices in the medical procedures.

Thermochromic liquid crystals (TLC) and other thermochromic materials have been used in medical applications to monitor the temperature of skin.

M. Parsley, "The Use of Thermochromic Liquid Crystals in Research Applications, Thermal Mapping and Non-Destructive Testing," *Semiconductor Thermal Measurement and Management Symposium,* 1991 SEMI-THERM VII, Seventh Annual IEEE Proceedings, 12-14 Feb. 1991, pp. 53-58 describes thermochromic liquid crystals.

U.S. Pat. No. 5,124,819 issued to Davis on 23 Jun. 1992 and entitled "Liquid Crystal Medical Device Having Distinguishing Means" describes a thermochromic device to detect skin temperature differences that may be associated with disease. A liquid crystal device has two layers of encapsulated thermochromic material for providing a color response with respect to temperature. The temperature ranges of color response of the two liquid crystal layers are different. A mechanism distinguishes the temperature range in which the device is operational. For example, a thermochromic strip may be fashioned into an elastic and deformable strip to monitor the temperature of a curved section of the body and detect disease states, such as cancer.

U.S. Pat. No. 4,649,923 issued to Hoffman on 17 Mar. 1987 and entitled "Temperature Indicating Electrotherapy Electrode" describes a temperature indicating electrotherapy electrode using liquid crystals. The temperature indicating electrotherapy electrode applies an electrical or electromagnetic signal to tissue of a living body and measures the physiological response of the tissue using the temperature responsive liquid crystal. The temperature indicating electrotherapy electrode is a small patch electrode that comprises a conductive metal foil used as a conductive patch electrode, the temperature responsive liquid crystal coated on the electrode, and a band of adhesive is provided around the outside of the electrode and liquid crystal layers. A color-temperature reference coating is provided as a border. A smaller sized electrode having this configuration is used relatively close to the treatment site with a larger dispersive return electrode used at a more remote location. In this manner, the arrangement ensures a higher density current at the treatment site and a lower, non-biologically stimulating signal at the larger electrode. The liquid crystal layer is sensitive to physiological temperature changes of 26° C. to 36° C., which includes the normal skin temperature range of 30° C. to 33° C. The small patch electrode may be used in therapies such as transcutaneous electrical nerve stimulation (TENS) in which electrical current is delivered to a patient through the small patch electrode and exits the patient through the larger dispersive electrode. The thermochromic layer is used to monitor the effectiveness of the delivered therapy. Such therapeutic electrodes are used to deliver very low intensity electrical energy (e.g., <0.1 watt) and cannot be used as a dispersive electrode during RF ablation. In RF ablation, high power (e.g., 20-300 watts) current is delivered. Using such an electrode in this application would lead to a high current density and subsequent skin burns due to the small electrode size. The low operating temperature range of these electrodes would result in the thermochromic layer changing colour in all cases when applied to the skin. This would make the electrodes unsuitable for detecting dangerous temperature elevations due to their lack of specificity.

Thus, a need clearly exists for a system of monitoring the temperature of a dispersive electrode at multiple sites during RF ablation to prevent burns being produced. The system must also be easy to monitor and able to detect dangerous temperature elevations with high sensitivity and specificity.

SUMMARY

In accordance with an aspect of the invention, there is provided a biomedical return electrode for electrosurgery or radiofrequency (RF) ablation. The electrode comprises: an electrode conductor for receiving electrical energy from tissue via a return path; and a thermochromic liquid crystal (TLC) layer coupled to the electrode conductor, the TLC layer changing colour at one or more sites dependent upon the temperature of the conductor at each site, the TLC layer changing colour in a predetermined range of temperatures from about 40° C. to about 50° C. to alert an operator about the risk of a burn occurring.

The electrical energy may comprise electrical current delivered through a surgical instrument, or a catheter. The electrical current may be delivered to tissue requiring treatment and the biomedical return electrode receives the electrical current via the return path.

The electrode conductor may be a thin conductive layer.

Preferably, the electrode conductor comprises metal. The metal may be aluminium.

The electrode conductor may be capacitively coupled with the tissue.

The biomedical return electrode may further comprise an electrical lead coupled to the electrode conductor for connection to an electrical device.

The TLC layer may be a single colour that changes colour at a predetermined temperature of 40° C.

The biomedical return electrode may further comprise TLC markings that indicate the state of the biomedical return electrode below a predetermined temperature. The TLC markings may be visible below a temperature of about 31° C. The TLC markings may become clear at a temperature of 31° C. or above. The absence of the TLC markings may indicate to the user that the biomedical return electrode has been damaged or deteriorated. The TLC markings may indicate whether or not the biomedical return electrode is adequately attached to tissue. The markings comprise one or more symbols.

The TLC layer may change colour to one of a plurality of colours.

The biomedical return electrode may further comprise different TLC markings that indicate the state of the biomedical return electrode above another predetermined temperature. The different TLC markings may visible at or above a temperature of about 50° C.

The biomedical return electrode may further comprise a mylar backing upon which the TLC layer is formed.

The biomedical return electrode may further comprise another TLC layer having an irreversible temperature change property to permanently indicate when a predetermined temperature is exceeded. The other TLC layer may comprise one or more TLC stripes. The one or more TLC stripes may be at least partially enclosed by an inert material to prevent diffusion. The inert material may comprise polyurethane.

The biomedical return electrode may further comprise: a photoconductive layer disposed between the TLC layer and the electrode conductor; and a plurality of ohmic connections coupled to the photoconductive layer that form an electrical connection if light is incident on the photoconductive layer. The TLC layer may be formulated to be opaque at room temperature become clear above a specific temperature. The TLC layer may be opaque at room temperature and becomes clear at 40° C. The photoconductive layer may comprise cadmium sulphide. An alarm may be triggered by the electrical connection. The biomedical return electrode may further comprise a reference cell for setting a threshold resistance.

A colour change of the TLC layer is preferably a binary colour change at a predetermined temperature. The colour change of the TLC layer is also preferably irreversible or permanent.

The TLC layer may comprise a plurality of strips partially covering the electrode conductor.

The TLC layer may partially cover the electrode conductor.

In accordance with another aspect of the invention, there is provided a biomedical electrode pad. The pad comprises: at least one biomedical return electrode in accordance with the foregoing aspects; and a conductive body coupled to the electrode to form a contact with tissue. The conductive body may be a jelly body. The biomedical electrode pad may further comprise a foam rubber peripheral body around the electrode and the conductive body.

In accordance with yet another aspect of the invention, there is provided a system, comprising: an apparatus for delivering electrical energy to tissue; and a biomedical electrode pad in accordance with the foregoing aspects coupled to the apparatus. The system may further comprising a colour sensor for viewing the biomedical electrode pad and monitoring equipment coupled to the colour sensor for remotely observing the biomedical electrode pad. The colour sensor may be a video camera In accordance with still another aspect of the invention, there is provided a method of treating tissue using a biomedical return electrode for electrosurgery or radiofrequency (RF) ablation. The method comprises the steps of: providing an electrode conductor for receiving electrical energy from tissue via a return path; and providing a thermochromic liquid crystal (TLC) layer coupled to the electrode conductor, the TLC layer changing colour at one or more sites dependent upon the temperature of the conductor at each site the TLC layer changing colour in a predetermined range of temperatures from about 40° C. to about 50° C. to alert an operator about the risk of a burn occurring Other aspects are implemented in accordance with the foregoing aspects of the biomedical return electrode, the biomedical electrode pad, and the system.

In accordance with a further aspect of the invention, there is provided an electrode for electrosurgery or radiofrequency (RF) ablation, comprising: an electrode conductor for conducting electrical energy; and a thermochromic liquid crystal (TLC) layer coupled to the electrode conductor, at least a portion of the TLC producing a visible change that is binary in character if the temperature of the electrode conductor exceeds a predetermined temperature in the temperature range of about 40° C. to about 50° C. to indicate the risk of a burn.

The visible change may comprise a binary colour change from a first colour to a second colour. The visible change may be irreversible or permanent.

The predetermined temperature may be about 40° C.

The electrode may further comprise a mylar backing upon which the TLC layer is formed.

In accordance with another aspect of the invention, there is provided method of providing an electrode for electrosurgery or radiofrequency (RF) ablation. The method comprises the steps of: providing an electrode conductor for conducting electrical energy; and providing a thermochromic liquid crystal (TLC) layer coupled to the electrode conductor, at least a portion of the TLC producing a visible change that is binary in character if the temperature of the electrode conductor exceeds a predetermined temperature in the temperature range of about 40° C. to about 50° C. to indicate the risk of a burn.

The visible change may comprise a binary colour change from a first colour to a second colour. The visible change may be irreversible or permanent.

The predetermined temperature may be about 40° C.

The electrode may further comprise a mylar backing upon which the TLC layer is formed.

BRIEF DESCRIPTION OF THE DRAWINGS

Embodiments of the invention are described hereinafter with reference to the drawings, in which:

FIG. 2A is a top plan view of a dispersive return electrode pad incorporating a TLC layer and having symbols displayed on its upper surface in accordance with another embodiment of the invention;

FIG. 2B illustrates the dispersive electrode pad of FIG. 2A placed on a patient's thigh to show an example of normal use of the electrode;

FIGS. 2C to 2E illustrate a simpler version of the TLC dispersive electrode pad with a single uniform TLC layer that changes colour above a predetermined temperature;

FIGS. 4A to 4E are plan views of a dispersive electrode pad in abnormal conditions;

FIG. 5 is a plan view illustrating the construction of the TLC-equipped dispersive electrode pad of FIGS. 4A to 4E;

FIGS. 6A to 6C illustrate an indelible quality assurance addition in accordance with a further embodiment of the invention;

FIG. 9 is a graph of the temperature data obtained during an animal experiment with a TLC electrode;

DETAILED DESCRIPTION

Figures 1A, 1B:
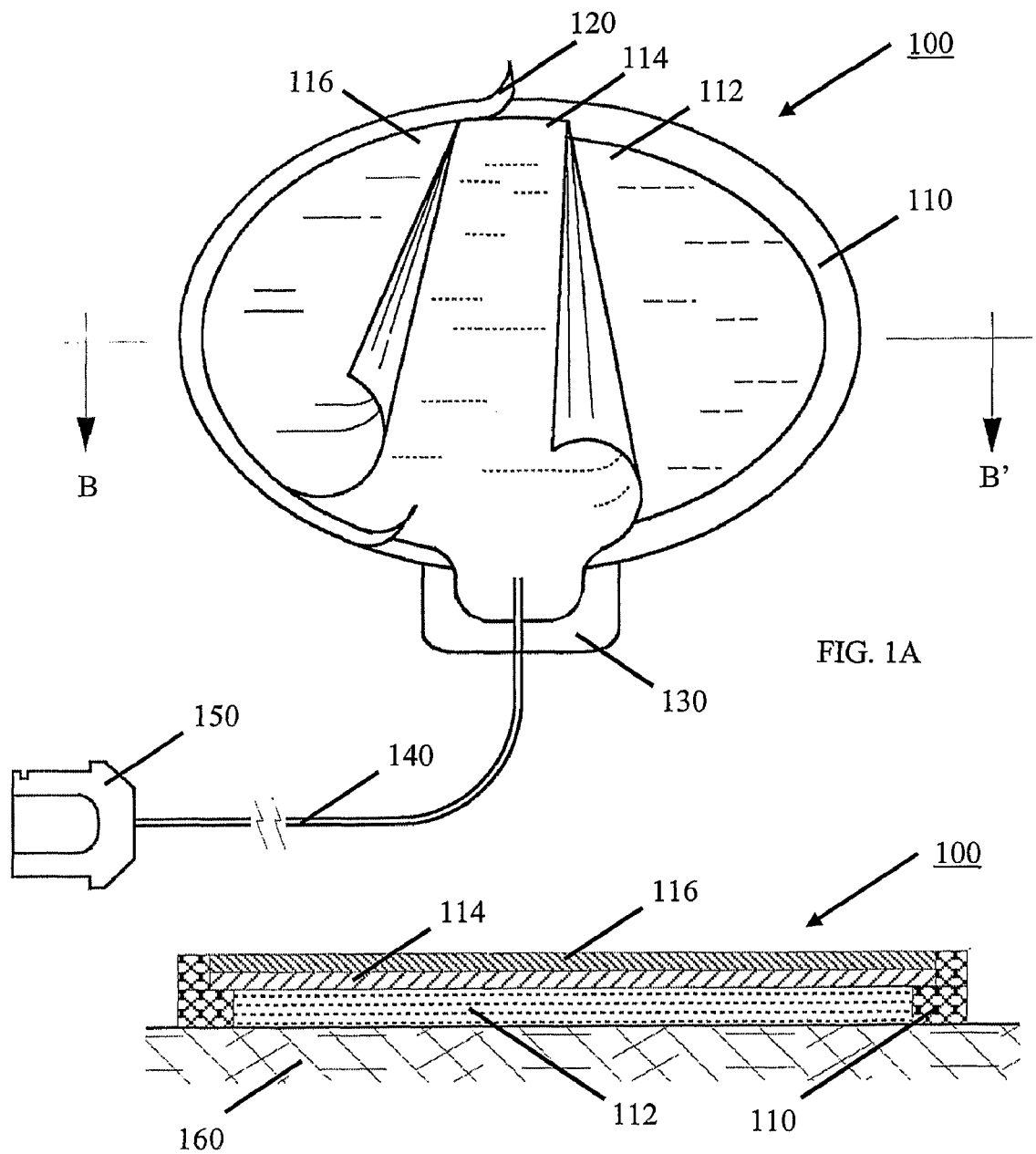
FIG. 1A is a top plan view of a dispersive return electrode pad incorporating a thermochromic liquid crystal (TLC) layer for displaying electrode (and hence patient skin) temperatures during RF ablation in accordance with an embodiment of the invention.
FIG. 1B is a cross-sectional, side view of the dispersive electrode pad of FIG. 1A.

Dispersive electrode pads and methods of making and using such pads are disclosed. In the following description, numerous specific details, including electrode materials, photoconductive materials, pad constructions, TLC formulations, colours, pad shapes, markings and/or symbols, ohmic connections, reference photoconductive cells and location of the same, and the like are set forth. However, from this disclosure, it will be apparent to those skilled in the art that modifications and/or substitutions may be made without departing from the scope and spirit of the invention. In other circumstances, specific details may be omitted so as not to obscure the invention. Where reference is made in any one or more of the accompanying drawings to steps and/or features, which have the same reference numerals or are specifically referred to as having similar numerals, those steps and/or features have for the purposes of this description the same function(s) or operation(s), unless the contrary intention appears.

I. Introduction

Burns associated with excessive heating at electrosurgical dispersive electrode pads are a serious complication of several surgical and percutaneous interventional procedures. To address this problem, the embodiments of the invention provide a dispersive electrode pad incorporating a thermochromic liquid crystal (TLC) layer that changes colour at sites of excessive heat to alert an operator of this hazard before a burn occurs. The dispersive electrode pad may be manufactured using relatively inexpensive materials and does not require any specialised equipment to monitor.

The embodiments of the invention enable monitoring of the temperature at a dispersive electrode using a thin layer of a thermochromic liquid crystal (TLC). Further, the embodiments of the invention enable an optional colour sensor to be used allowing the colour of the pad to be monitored and displayed remotely.

The addition of a TLC layer allows temperature to be measured over the entire surface of a dispersive electrode at high spatial resolution (>1000 points). Further, the TLC material is relatively inexpensive and readily available. For example, the commercial prices of fully prepared TLC sheets suggest that the addition of a TLC layer to a dispersive electrode would only nominally increase the cost of the electrode (e.g., AU$1). Advantageously, dispersive electrode pads equipped with TLC layers do not require any special equipment to monitor them. Monitoring of the visual appearance of a dispersive electrode during and after ablation current delivery may be incorporated into the routine nursing observations, for example.

The TLC pads in accordance with the embodiments of the invention have been tested in a sheep model. Pads constructed with a 45-50° C. temperature TLC sheet (R45C5W, B & H Liquid Crystal Resources, Riverside Buildings, Dock Road, Connah's Quay, Deeside, Flintshire, CH5 4DS, United Kingdom) have detected temperature rises associated with the partial application of the return pad. The burns associated with partial application of the pad are clearly predicted by an area represented by green and higher TLC colouring. In clinical cases, such burns obviously may be avoided, by choosing a TLC layer that provides an early warning at a temperature of 40° C.

The TLC equipped return pads may also be used in a research and product development setting to study the patterns of heat build up under return pads during ablation procedures.

II. Dispersive Return Electrode

FIG. 1A is a top plan view of a dispersive return electrode pad 100 in accordance with an embodiment of the invention. The electrode pad 100 incorporates a thermochromic liquid crystal (TLC) layer 116 for displaying patient temperatures during RF ablation. In this example, the overall shape of the pad 100 is oval, however, many other shapes may be practiced including square, rectangular, circular, trapezoidal, and the like, without departing from the scope and spirit of the invention. For ease of description, the pad 100 is explained with reference to both FIGS. 1A and 1B, where FIG. 1B is a cross-sectional, side view of the dispersive electrode pad 100. The dispersive electrode pad 100 comprises a TLC sheet, a conductive layer, and an adhesive and conductive gel to attach the pad to the patient.

The electrode pad 100 has a foam rubber peripheral body 110, enclosing an electrode jelly body 112 that contacts the body 160 of a patient. The peripheral body 110, which may have an annular shape, provides support for the electrode and prevents the electrode gel from dispersing laterally. The jelly body 112 is highly conductive and ensures a good contact between the patient's body and the fall surface area of the conductive layer. However, numerous other conductive materials may be practiced, such as a conductive foam sponge, for example. Other methods of transferring electrical energy such as capacitive coupling of the conductive element to the patient's skin may also be practiced The gel layer 112 is preferably adhesive, highly conductive and conformable to allow the dispersive electrode pad 100 to be attached to the patient.

On top of the electrode jelly body 112 and preferably over an internal lip of the peripheral body 110 is disposed a conductive material sheet 114, which may be adhered to the peripheral body 110, for example, using a contact adhesive (eg Norton Contact Cement). This sheet 114 is the electrode conductor and may be constructed of a thin layer of metal. In one embodiment of the invention, the conductive metal sheet 114 is aluminium foil, however, numerous other conductive materials may be practiced without departing from the scope and spirit of the invention. For example, copper, silver, tin, platinum or gold foils may be practiced.

The electrode conductor layer 114 is connected electrically to a connector or socket 150, which can be attached to the return pole of an ablation current generator. An electrical lead 140 is connected to a rectangular tab portion of the aluminium foil 114 at one end and the connector 150 at an opposite end. The rectangular tab portion of the foil 114 is supported and enclosed by a substantially rectangular extension 130 of the foam rubber peripheral body 110 to support the tab portion and provide electrical insulation.

A TLC layer 116 is disposed on top of the aluminium foil 114. To allow the TLC temperature change to be easily seen, the TLC layer 116 may be microencapsulated and sprayed onto a thin backing layer or sprayed directly onto the conductor 114 in an appropriate manner. The TLC material may be a cholesteric material (e.g., cholesteryl pelargonate, cholesteryl chloride, oleyl cholesteryl carbonate and others). The thin backing layer may be mylar, for example. The TLC layer 116 may be adhered to the aluminium foil 114 using a contact cement. An annular ring of adhesive backed tape 120 covers the edge of the TLC layer 116 and the conductor 114 relative to the foam rubber peripheral body 110.

The TLC layer 116 is constructed so that this layer 116 does not change colour until the layer 116 is warmer than the temperature range that is usually recorded at the dispersive electrode (e.g., approximately 40° C. as the temperature usually is less than 40° C. during normal dispersive pad operation). The TLC layer 116 preferably has a broad temperature-operating band of ~10° C. to reduce false negative responses due to the TLC exceeding its operating temperature.

Thus, FIGS. 1A and 1B illustrate a biomedical electrode pad 100 that comprises a biomedical return electrode for electrosurgery or radiofrequency (RF) ablation. The electrode conductor 114 can receive electrical energy from tissue via a return path. The TLC layer 116 is coupled to the electrode conductor 114 and changes colour at one or more sites dependent upon the temperature of the electrode conductor 114 at each site. The TLC layer 116 changes colour in a predetermined range of temperatures from about 40° C. to about 50° C. to alert an operator about the risk of a burn occurring. A return electrode typically has a large geometry compared to other electrodes. For example, such a return electrode may have dimensions of 16 cm×9.5 cm. A variety of geometries may be employed besides the oval configuration shown in FIG. 1A. The size of the electrode is important to dispersive electrodes. In other circumstances, a return electrode may have smaller size if specially adapted in turns of configuration for capacitance. Normal temperature ranges for skin are 26° C. to 36° C. In contrast to looking for small temperature changes as might employed in TENS measurements, larger temperature changes are detected in the biomedical return electrode according to the embodiments of the invention. Good spatial resolution is required. The TLC layer must cover effectively the entire electrode. In one particular embodiment, binary colours may used. This would indicate that the temperature at the site had reached a dangerous or negative level. For example, at 40-41° C., a binary colour change may occur at the site.

As the thermochromic dispersive electrode 100 will be used as the return path for the current, the electrode connector must be securely attached to the conductor. This is because any interruption to this connection would lead to the current leaving the patient through another connection (e.g., ECG lead connectors). These other connections are generally not designed to function as dispersive electrodes and therefore the patient is likely to suffer a burn underneath these connections.

In alternative embodiments of the invention, the TLC layer may comprise a plurality of strips partially covering electrode conductor. For example, the stripes may be configured to run in a spaced apart parallel configuration across the surface of the electrode conductor. Alternatively, the stripes may be crisscrossed to form a grid-like pattern covering the surface of the electrode conductor. Other variations of patterns of stripes may be practiced. In yet another embodiment of the invention, the TLC layer may partially cover electrode conductor. For example, the TLC layer may be formed of a number of concentric annular rings covering portions of the surface of the electrode conductor. Other partial TLC layers may be practiced without departing from the scope and spirit of the invention.

III. Alternate Embodiment of Dispersive Return Electrode

In accordance with another embodiment of the invention, the TLC layer is disposed on top of the aluminium foil. To allow the TLC temperature change to be easily seen, the TLC layer may be microencapsulated and sprayed onto a thin backing layer or sprayed directly onto the conductor in an appropriate manner. The TLC material may be a cholesteric material (e.g., cholesteryl pelargonate, cholesteryl chloride, oleyl cholesteryl carbonate and others). An example of Chiral Nematic Liquid Crystals that may be used is given by the following general chemical formulae:

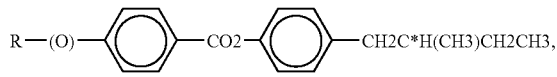

(1)

where R=n-alkyl and * denotes a chiral centre. Further details of TLC materials can be found in M. Parsley, "The Use of Thermochromic Liquid Crystals in Research Applications, Thermal Mapping and Non-Destructive Testing," *Semiconductor Thermal Measurement and Management Symposium*, 1991 SEMI-THERM VII, Seventh Annual IEEE Proceedings, 12-14 Feb. 1991, pp. 53-58. The thin backing layer may be mylar, for example. The TLC layer may be adhered to the aluminium foil using a contact cement. An annular ring of adhesive backed tape 120 covers the edge of the TLC layer and the conductor relative to the foam rubber peripheral body.

The TLC layer is constructed so that this layer does not change colour until the layer is warmer than the temperature range that is usually recorded at the dispersive electrode (e.g., approximately 40° C. as the temperature usually is less than 40° C. during normal dispersive pad operation). The TLC layer preferably has a binary colour change at or about 40° C. (eg. Hallcrest G40C). This TLC material therefore change colours from green to transparent at 40° C., for example. If the TLC material has a black backing layer, the observed colour is green at regions below 40° C. and black at regions greater than 40° C. This binary colour change is therefore simple for even inexperienced staff to interpret (trainee staff can be instructed that the dispersive electrode should be a green colour and that the presence of any black colouration indicates a dangerous situation). Clearly, other choices of colours can be practiced without departing from the scope and spirit of this invention. Green has been chosen as the base colour because this is generally perceived as a colour indicating safety or the absence of any abnormalities. Black has been chosen as the alternating colour, because it has a high contrast with green and should be clearly visible even if the observer is colour blind. For this reason, a change of colour between red and green may be less desirable, because colour blind observers may not be able to detect a change in colour. More preferably, the colour change produced in the TLC layer is irreversible or permanent. Thus, if the temperature has been exceeded at a site, a permanent colour change occurs at the site. This provides a permanent indication of the potential burn site to a clinician, who might have overlooked or missed a transient colour change.

Other variations and configurations of the return electrode and electrode pad may be practiced with the binary TLC, as well as the irreversible or permanent binary layer, in accordance with the embodiments of the invention described hereinbefore and hereinafter.

IV. TLC Colour Sensing System

Figure 3:
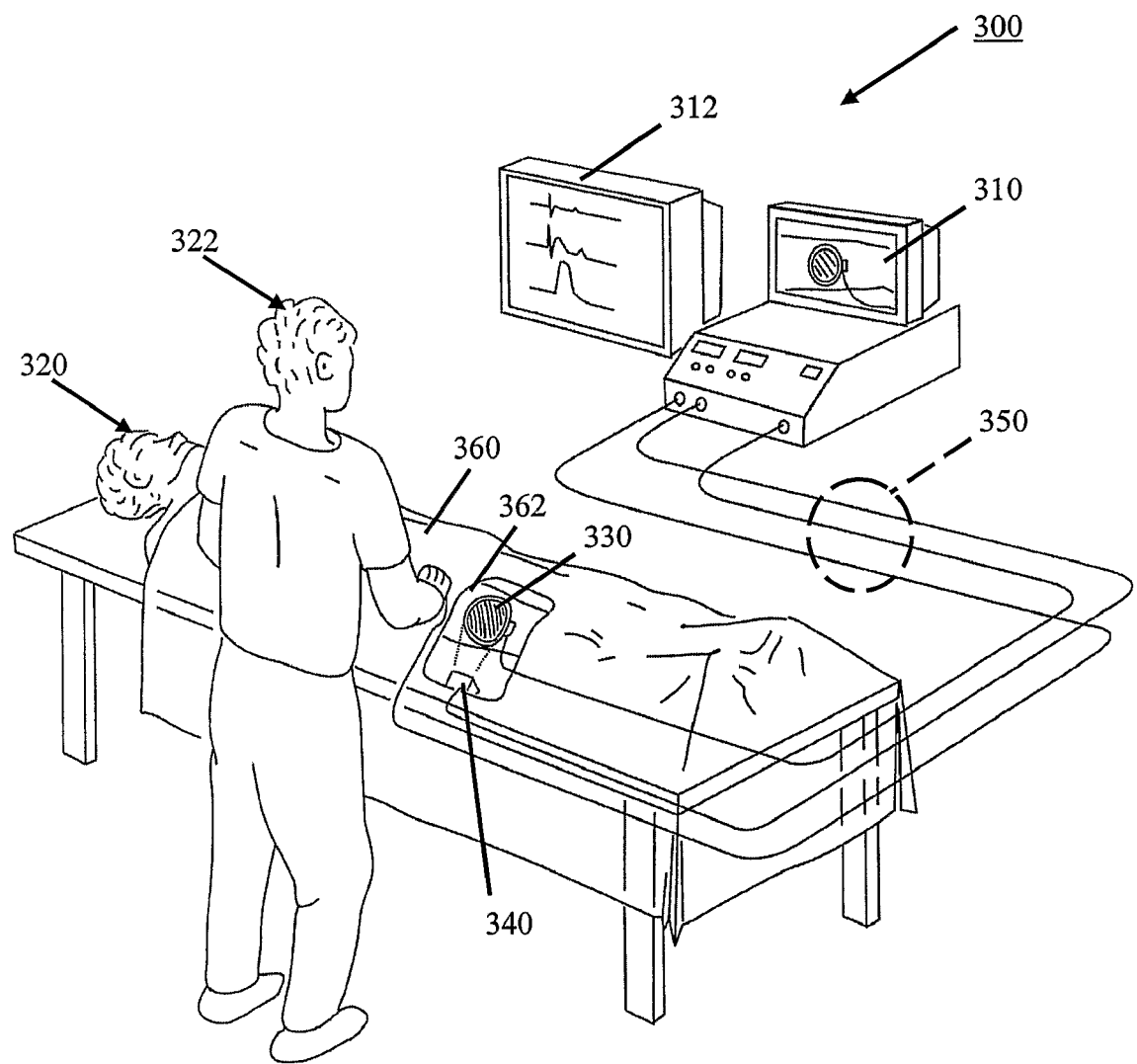
FIG. 3 is a perspective view of a patient in an operating theatre with the electrode pad in situ on the patient's thigh and an optional colour sensor allowing the colour of the pad to be displayed remotely for monitoring by the surgeon.

In clinical use, the TLC-equipped dispersive electrode pad 100 should be regularly monitored as part of the routine medical observations during and after radiofrequency ablation or delivery of electrosurgery current. For example, this function might be performed as part of normal nursing observations. FIG. 3 illustrates a patient 320 in an operating theatre 300 with the TLC-equipped electrode pad 330 in situ on the patient's thigh. An aperture 362 may be provided in a sheet 360 covering the patient 320, so that an observer 322 (e.g., a doctor, nurse, and/or other medical staff) can directly observe the electrode pad 330. Alternatively, the sheet 360 covering the patient may comprise a transparent window (e.g., made of plastic) permitting the observer 322 to directly view the electrode pad 330. The operating theatre 300 may be equipped with monitoring equipment and RF generator 310 and other medical equipment 312.

Optionally, a colour sensor 340 (e.g., a video camera and appropriate light source) may be oriented to view the TLC-equipped electrode pad 330 and coupled by suitable electrical leads 350 to monitoring equipment and RF generator 310 (e.g., the monitoring equipment may be a standard video monitor, a television, a computer screen, or other suitable display device). The electrical leads 350 may include an electrical cable for the camera 340, an ablation catheter, and patient return electrode cable. This arrangement enables the observer 322 to observe the TLC-equipped electrode pad 330, and in particular its colour, on a conveniently located monitoring equipment 310, e.g. so that the observer 322 does not have to bend or twist the observer's head or body position to view the pad 330. The monitoring equipment 310 may be positioned remotely relative to the electrode pad 330. For example, the colour sensor may be a CCD sensor that is coupled to a computer, relaying digital images to the computer. The computer may execute image processing techniques well known to those skilled in the art to segment the image and identify any changes in colour of the TLC layer indicated in the digital image. Such image processing techniques may be embodied in software, including computer programs. This may be done automatically to trigger an alarm to alert users of a potential burn occurring to tissue at the biomedical return electrode.

V. Dispersive Return Electrode with Markings

In another embodiment of the invention, the dispersive electrode pad 100 of FIG. 1 may have safety markings on the TLC-layer 116. FIGS. 2A and 2B FIG. 2A illustrate such a dispersive electrode pad 200 incorporating two TLC layers 216, where one TLC layer has markings (e.g., symbols) displayed on its upper surface. FIG. 2B illustrates the dispersive electrode pad 200 in situ on a patient's thigh during normal use of the electrode pad 200. Save as to the markings and the two TLC layers 216, the dispersive electrode pad 200 of FIG. 2 is similarly constructed to that of FIG. 1, where corresponding numbers are used except for the first digit (e.g., the TLC layer 116 has the counterpart TLC layers 216 in FIG. 2A).

The dispersive electrode pad 200 has visible markings (e.g., question marks) when removed from the packaging (not shown) in which it is stored initially. For example, when the wrapper enclosing the pad 200 is removed, the TLC layers 216 of the pad 200 may generally appear black with yellow "?" markings or symbols appearing across its surface. This would be the case where the pad 200 is initially at room temperature (i.e., not above normal ambient temperatures). Other colours of the TLC layers, symbols and/or markings, and marking colours may be practiced without departing from the scope and spirit of the invention. This variation of the electrode pad addresses quality control issues. A separate layer of TLC shows colour (e.g., yellow) at room temperature and becomes clear at patient temperatures (e.g., 31° C.). If the electrode pad 200 is damaged or deteriorates in storage, transit, or otherwise (e.g., by exposure to heat or ultraviolet radiation), the colour of the markings is not visible when the pad 200 is removed from the packaging, indicating a problem. Further, the adequacy of the pad attachment to the patient can be assessed, as the colour does not disappear when the pad 200 is attached to the patient, but remains or reappears in those parts of the pad 200 that poorly contact the patient.

FIG. 2B illustrates an arrangement 250 of the TLC-equipped dispersive electrode pad 200 positioned on a patient's thigh 260 and in good contact with the patient. Initially, when positioned on the patient's thigh 260, the pad 200 at ambient temperature appears as depicted in FIG. 2A with the markings in one TLC layer 216 visible. After a short period on the patient's thigh 260 (e.g., a few seconds), the pad 200 warms to the temperature of the patient's skin (e.g., greater than 31° C.), and the markings are no longer readily visible (the "?" symbols disappear) at skin temperature. The pad 200 may appear uniformly black, assuming the background colour of the other TLC layer is normally black. Once the TLC layers 216 of the pad 200 appear uniformly black, the pad 200 is ready for use in the medical procedure and should remain black throughout the procedure in normal use.

FIGS. 2C to 2E represent the appearance of a simple "Good/Bad" TLC-equipped dispersive electrode 270. There is one TLC layer that initially appears one uniform colour (e.g., green or another appropriate colour) in normal use, as shown in FIG. 2C. If any part of the electrode is heated above 40° C., that part 272 changes colour to an alternative colour (e.g., red or another contrasting colour) to give an unambiguous indication that the pad needs attention, as shown in FIG. 2D. FIG. 2C shows the enlarged part 274 that has changed colour. This variation of the pad 270 has the advantage of being easier to manufacture and easier to interpret for the less skilled user.

VI. Dispersive Return Electrode with Multiple TLC Layers and Markings

FIG. 4 illustrates the appearance of the pad 400 (corresponding to the pad 200 of FIG. 2, but having yet another TLC layer with the symbols "H") in abnormal conditions. FIG. 4A shows the pad 400 where the pad 400 is partially detached in the lower right corner of the pad, where at least portions of the symbols "?" are clearly visible. Because the pad is partially detached, the detached portion cools below 31° C. and the "?" symbols appear. The upper left portion 402 is well contacted to the patient as indicated by the solid colour of the other TLC layer. The lower right portion of the pad 400 is becoming detached and would need to be brought back into good contact with the patient.

FIG. 4B illustrates an abnormal condition where heating is occurring in a portion 410 of the pad 410 located in the upper left corner. This portion 410 of the pad 400 is shown as white for ease of depiction, but the actual colour may be red. Thus, the TLC layer turns red indicating a hot spot (e.g., 40° C.). In FIG. 4C, the TLC layer becomes green at the location 420 (410 in FIG. 4B) as the temperature reaches 44° C. For ease of depiction, green is indicated by diagonal line hatching having a first spacing between lines. The actual red area 422 (e.g., 40° C.) spreads outwardly, again indicated by white fill in FIG. 4C.

In FIG. 4D, the area 430 (corresponding to areas 410, 420) turns the actual colour blue at the hottest area (e.g., >52° C.). The marking "H" appears where any part of the pad 400 exceeds 50° C. This is achieved using a further TLC layer. The areas 432, 434 of temperatures 46° C., 45° C. spread outwardly. FIG. 4E illustrates the pad 400, where the TLC layer returns to the actual colour black in the hottest region 440, while the other areas 442, 444, and 446 spread. The "H" mark areas 440, 442 have increased in size in FIG. 4E.

The construction of the TLC-equipped dispersive electrode pad 400 is explained with reference to the TLC layer shown in FIG. 5. Initially, the pad 500 has a 31° C. TLC formulation sprayed through a markings/symbol mask onto mylar or other appropriate flexible non-conducting layer to form the layer 510. In the example of FIG. 5, this layer 510 involves a mask with "?" symbols (reversed in the example because it is sprayed onto the patient side of the mylar layer, and indicated by solid filled symbols on a white background representing the mylar). This TLC formulation may for example be coloured red or yellow so that red or yellow markings are visible below 31° C., but be clear at or above that temperature. A 40-50° C. TLC formulation is then sprayed onto the mylar for the layer 512, indicated by diagonal hatching lines superimposed on the "?" symbols. This formulation is clear below 40° C. and progresses through actual colours red, green, and blue, before turning clear again above 58° C. Note that the clearing temperature for most commercially available TLC formulations tends to be several degrees higher than the specified (red-mid green) temperature range. A 50-60° C. TLC formulation is sprayed onto the mylar through another markings/symbols mask (e.g., "H") to provide the layer 514. This formulation is clear below 50° C. and progresses through red, green, and blue before turning clear again above 70° C. A black backing paint is sprayed on the mylar to form the TLC layer 500 of the electrode pad. While specific temperature ranges for TLC formulations, symbols/markings, colours, and numbers of layers are set forth for this embodiment, it will be apparent to one skilled in the art in view of this disclosure that numerous changes and/or substitutions may be made without departing from the scope and spirit of the invention.

VII. Dispersive Return Electrode with Irreversible TLC Material

Another embodiment of the invention is depicted in FIGS. 6A to 6C, which provides indelible quality assurance. Some TLC materials (e.g., Thermax S C, B & H Liquid Crystal Resources, Riverside Buildings, Dock Road, Connah's Quay, Deeside, Flintshire, CH5 4DS, United Kingdom) have an irreversible temperature change property. Using such a TLC material with such properties, a electrode dispersive pad may be practiced that permanently demonstrates if the temperature of any part of the pad has ever reached elevated or dangerous levels. This information would be useful in the event that a burn does occur in a patient.

FIG. 6A shows the underside of a dispersive electrode pad 600, with a portion 620 of the pad magnified in FIG. 6B. The underside of the pad 600 shown in FIG. 6B includes an area 612 that has not been excessively heated (e.g., T<45° C.), indicated by diagonal hatching, and an area 610 that has been hot (e.g., T>45° C.), indicated by solid white fill. FIG. 6C is a side cross-sectional view along the line depicted in FIG. 6B, of about 4 mm, across cool and hot regions 610, 612. The top layer 670 of this portion 620 is a TLC layer(s). Beneath this layer 670 is an aluminium electrode 660. Under the aluminium electrode 660 are quality assurance TLC stripes 650, 652 in a polyurethane mask. The TLC stripes 650, 652 may be located between the aluminium electrode 660 and the gel body 640 attached to the patient's skin 630. The TLC stripe 650 has solid hatching, indicating that the stripe 650 has not been heated above 45° C., i.e. in the cool region 612. In contrast, the TLC stripe 652 is clear, indicating that the stripe 652 has been heated above 45° C., i.e. in the hot region 610.

To form the stripes 650, 652, the lower surface of the aluminium electrode 660 may be sprayed with thin stripes of a TLC formulation that is black, or another appropriate colour, below 45° C. and clear at or above 45° C. The TLC formulation is irreversible, i.e. it does not change back to black when it cools. The stripes 650, 652 may then be masked with a clear spray (e.g., polyurethane, clear lacquer or plastic coating) to prevent the TLC material from diffusing into the gel body 640 during storage. In use, the stripes 650, 652 are either black (indicating the pad has not been heated excessively) or clear (indicating that portion of the pad has been heated above 45° C.). The stripes 650 are not normally seen, being visible through the gel body 640 after the pad 600 is removed from the patient 630. The non-reversing TLC formulation allows for quality assurance examination of the pad after use.

VIII. Dispersive Return Electrode with Light Gate

Figure 7A:
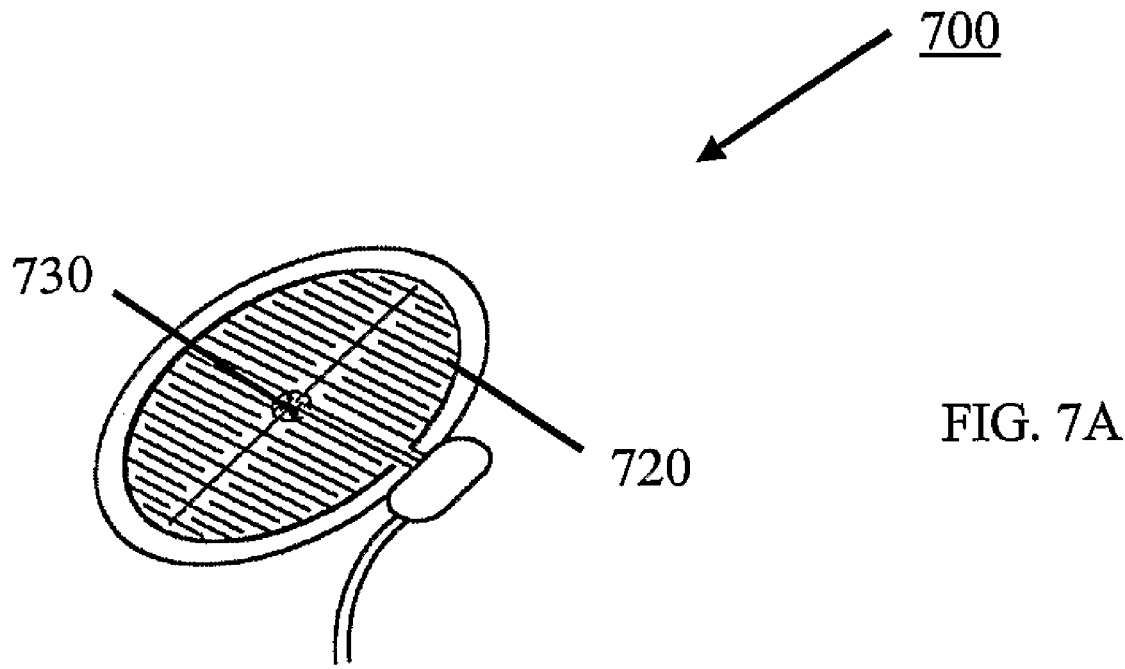
FIG. 7A is a perspective view of ohmic connections to a photoconductive layer, where the TLC layer is used as a light gate for an alarm.
Figure 7B:
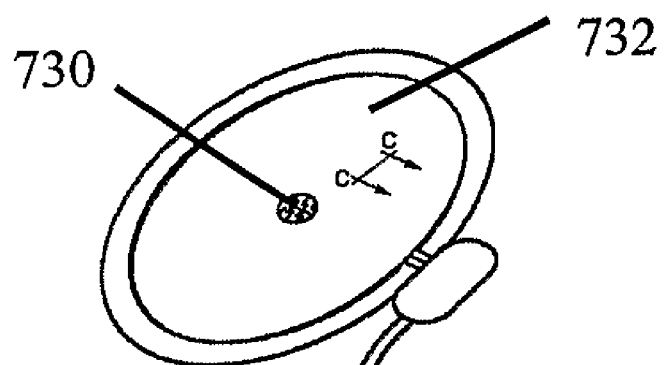
FIG. 7B is a perspective view of the TLC layer on top of the photoconductive layer, with a hole for a photoconductive reference cell.
Figure 7C:
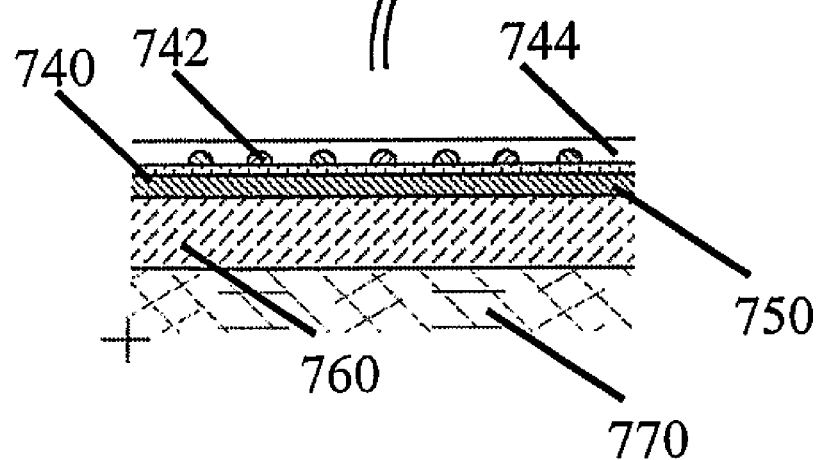
FIG. 7C is a cross-sectional, side view through the dispersive electrode pad of FIGS. 7A and 7B.

FIGS. 7A to 7C depict a TLC layer used as a light gate for an alarm in accordance with yet another embodiment of the invention. This embodiment addresses the problem that the pad 700 must be observed continuously during ablation in order to detect abnormal heating at any part of the pad. FIG. 7A shows ohmic connections 720 to a photoconductive layer, with a reference photoconductive cell 730 in the center. The ohmic connections 720 may be any highly conductive material, such as wires. The wires do not touch, and the photoconductive layer is between the wires. The photoconductive layer 740 has a high resistance when there is no light incident upon it, but becomes conductive when light is shown on it. FIG. 7B shows a TLC layer 732 on top of the photoconductive layer. The hole 730 is for the reference photoconductive cell. FIG. 7C shows a side cross-sectional view of the electrode pad 700 along the line C-C of FIG. 7B. The top layer is a TLC layer 732. A number of ohmic connections 742 are formed between the TLC layer and a photoconductive layer 740. Beneath the photoconductive layer 740 is the aluminium electrode 750, which is attached to a conductive gel body 760 on a patient's skin 770.

The surface of the aluminium electrode 750 may be sprayed with a photoconductive layer 740 (e.g., cadmium sulphide, selenium, thionaphthenindole or a similar material). Preferably, the photoconductive layer has a high electrical resistance if the layer is not exposed to light and a low electrical resistance if exposed to light. The ohmic connections 742 are made to the photoconductive layer 740 and to the reference photoconductive spot 730, which may be set in the centre 730 of the pad 700. Over this layer 740 with contacts 742, the TLC layer 744 may be sprayed which has a clearing temperature of 45° C.

In use, the photoconductive layer 740 has a high resistance because the TLC layer 744 prevents light from reaching the layer 740. When any part of the pad 700 reaches 40° C. or higher, the relevant portion of the TLC layer 744 clears and allows light to reach the photoconductive layer 740. The resistance of this layer 740 decreases below a threshold set by the reference cell 730, triggering an alarm. Thus, if part of the pad 700 becomes hot, the operator is able to see a change in colour at the relevant area if the person is observing the pad 700. However, even if the person is not observing the pad 700, an alarm coupled to the electrode pad and the ohmic connections 742 can be triggered (e.g., the alarm may sound if it is an audible alarm), because the photoconductive layer reduces in resistance, completing the alarm circuit. Alternatively, the alarm circuit may reduce or abolish the power delivered by the RF generator to prevent the patient sustaining a burn.

IX. A Method of Treating Tissue

Figure 8A:
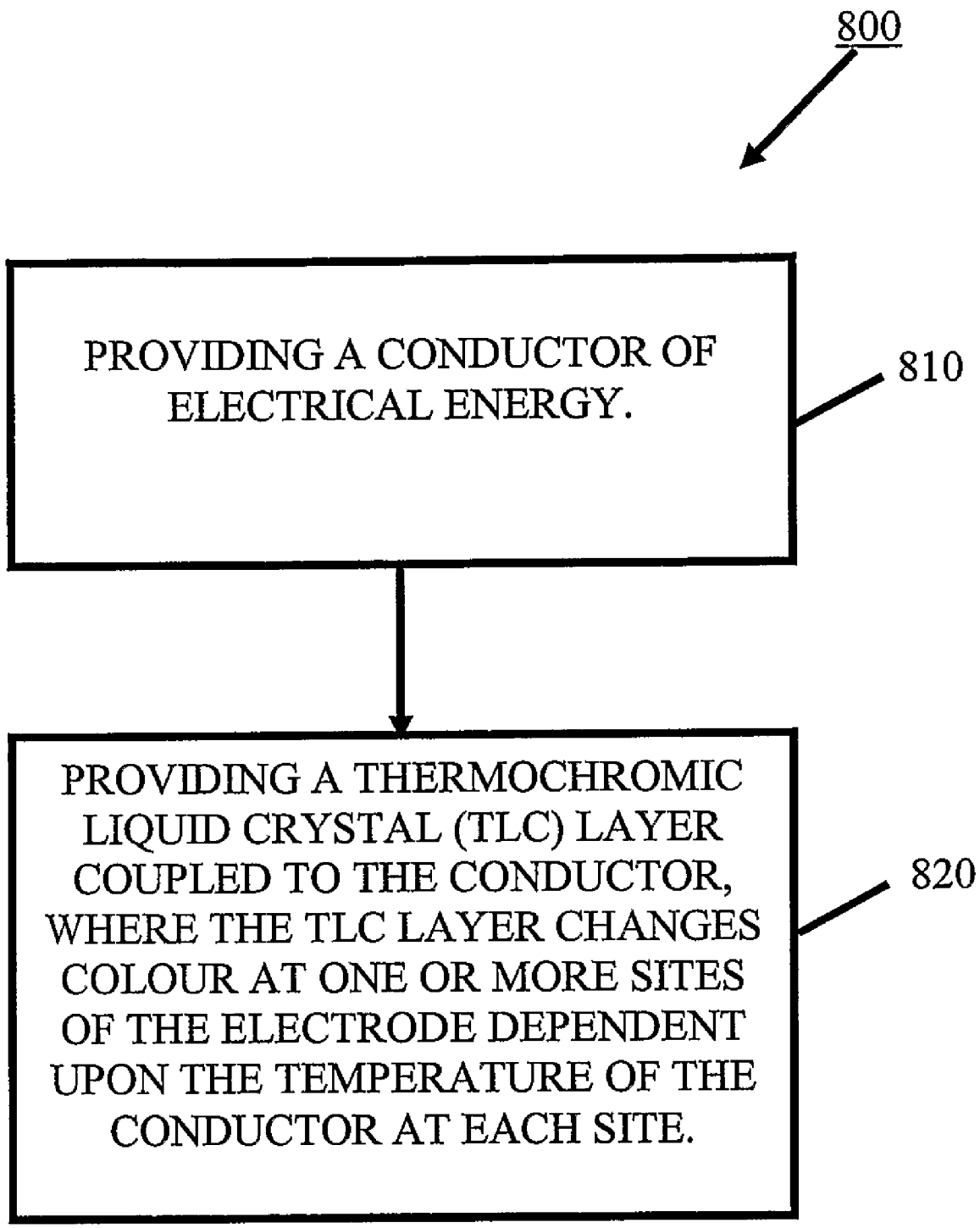
FIG. 8A is a high-level flow diagram of a method of treating tissue using an electrode in accordance with another embodiment of the invention.

FIG. 8A illustrates at a high level a method 800 of treating tissue using an electrode. In step 810, a conductor of electrical energy is provided. The electrode may be a biomedical electrode, such as can be used in surgical and percutaneous interventional procedures involving electrosurgical or radiofrequency (RF) ablation techniques. The conductor may be made of metal, such as aluminium; however, other conductive materials may be practiced without departing from the scope and spirit of the invention. The conductor is preferably arranged as a thin conductive layer. In step 820, a TLC layer coupled to the conductor is provided. The TLC layer changes colour at one or more sites of the electrode dependent upon the temperature of the conductor at each site. The TLC layer may provide colour change to alert an operator about the risk of a burn occurring. This occurs in a predetermined range of temperatures, which may be about 35° C. to about 45° C. The TLC layer may change colour to any one of several colours.

Figure 8B:
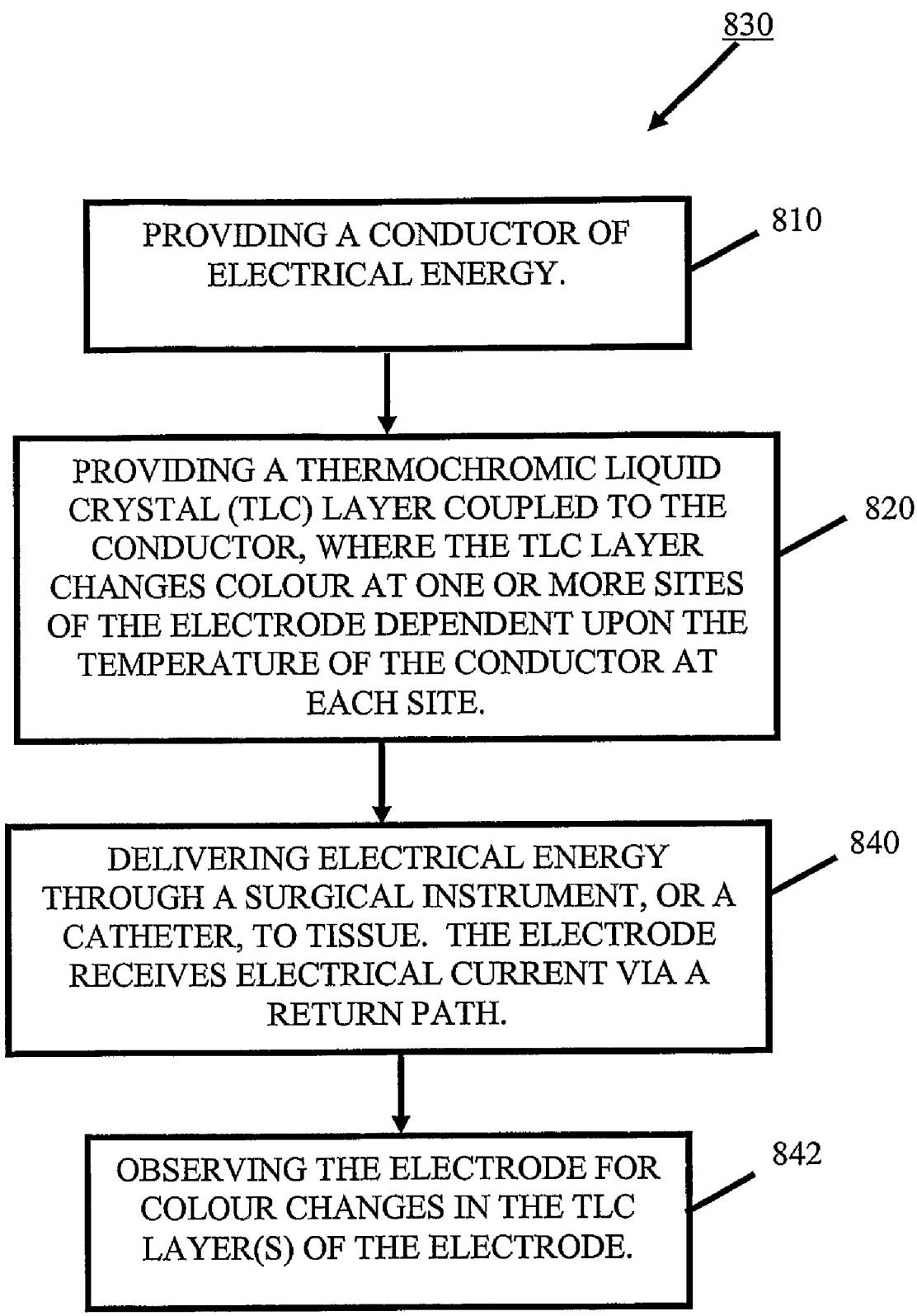
FIG. 8B is a more detailed flow diagram of the method of FIG. 8A illustrating further steps that may be performed.

FIG. 8B is a detailed flow diagram of a method 830 of treating tissue using the electrode. Processing is carried out in steps 810 and 820 in the manner of method 800. In step 840, electrical energy is delivered through a surgical instrument, or a catheter; the electrical energy comprises RF electrical current. The electrode receives the electrical current via a return path. The electrical energy may be delivered to tissue using an apparatus for delivering such electrical energy. In step 842, the electrode is observed for colour changes in the TLC layer(s) of the electrode.

X. Another Method of Treating Tissue

Figure 10:
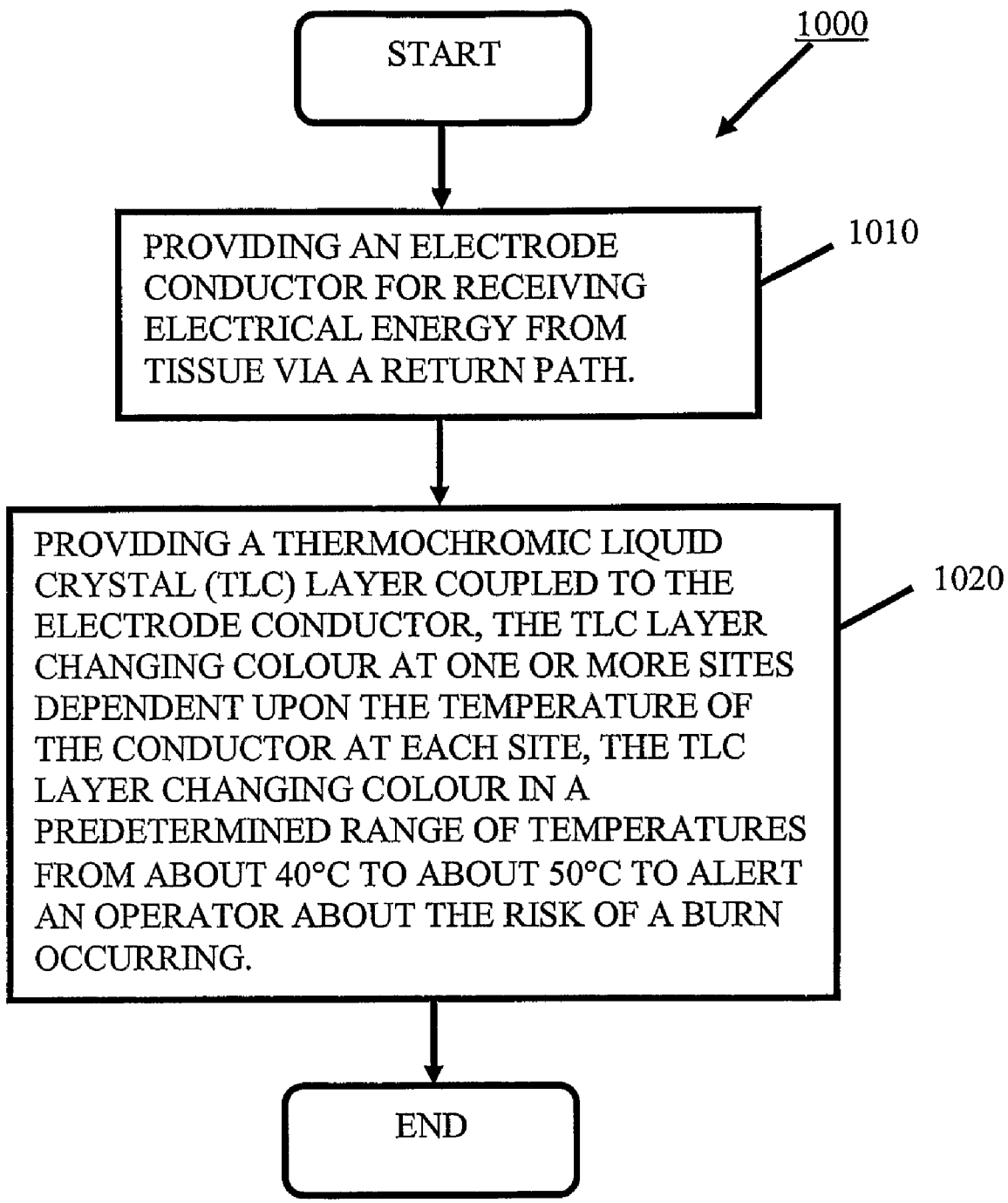
FIG. 10 is a flow diagram of a method of treating tissue using a biomedical return electrode for electrosurgery or radiofrequency (RF) ablation.

FIG. 10 is a flow diagram of a method 1000 of treating tissue using a biomedical return electrode for electrosurgery or radiofrequency (RF) ablation. In step 1010, an electrode conductor is provided for receiving electrical energy from tissue via a return path. In step 1020, a thermochromic liquid crystal (TLC) layer is provided coupled to the electrode conductor. The TLC layer changes colour at one or more sites dependent upon the temperature of the conductor at each site. The TLC layer changes colour in a predetermined range of temperatures from about 40° C. to about 50° C. to alert an operator about the risk of a burn occurring. The method then terminates.

XI. Method of Providing an Electrode for Electrosurgery

Figure 11:
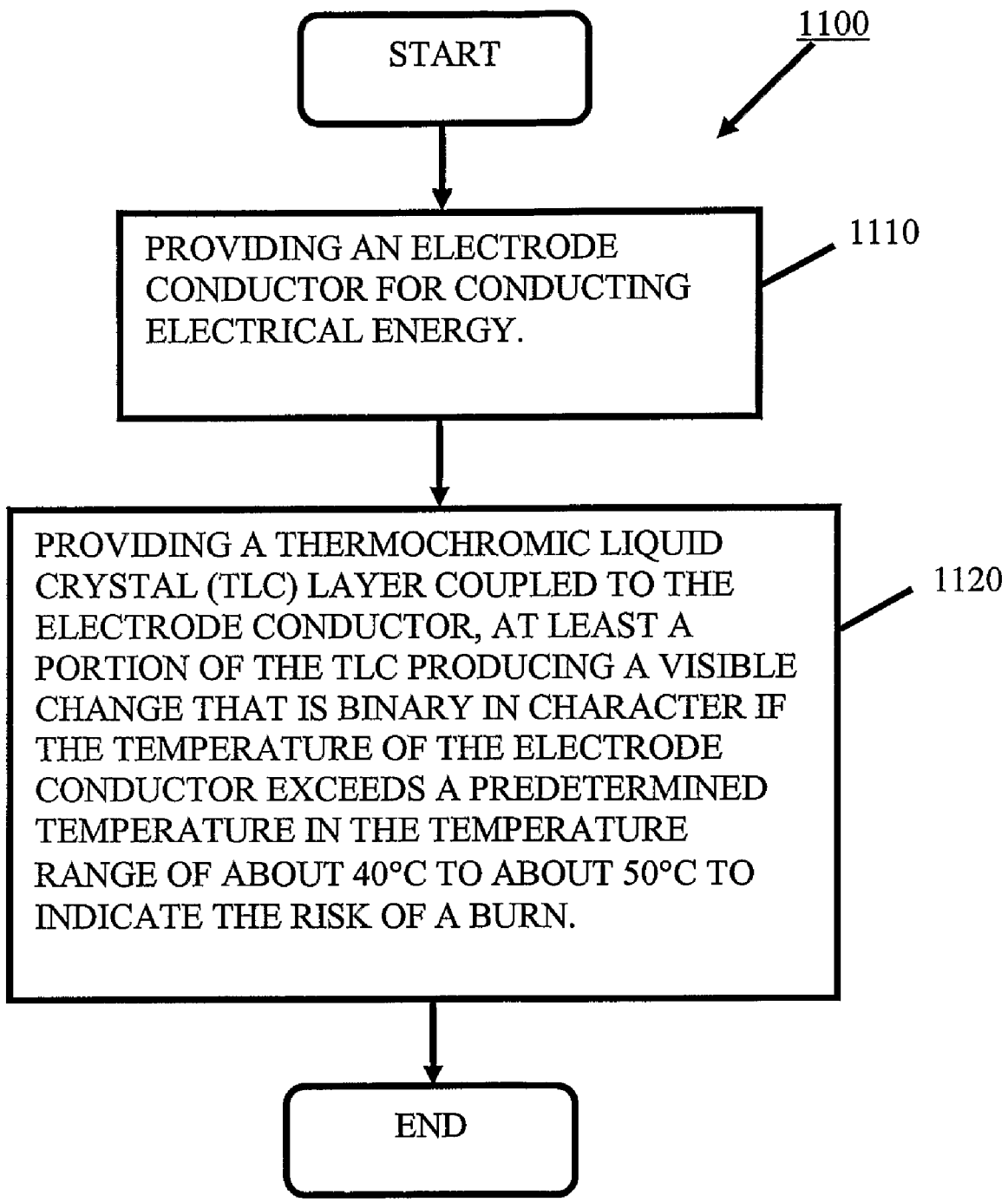
FIG. 11 is a flow diagram of a method of providing an electrode for electrosurgery or radiofrequency (RF) ablation.

FIG. 11 is a flow diagram of a method 1100 of providing an electrode for electrosurgery or radiofrequency (RF) ablation.

In step 1110, an electrode conductor for conducting electrical energy is provided. In step 1120, a thermochromic liquid crystal (TLC) layer coupled to the electrode conductor is provided. At least a portion of the TLC layer produces a visible change that is binary in character if the temperature of the electrode conductor exceeds a predetermined temperature in the temperature range of about 40° C. to about 50° C. to indicate the risk of a burn. For example, the predetermined temperature may be 40° C. or 41° C. The method then terminates.

XII. Clinical Data and Alternate Embodiments

FIG. 9 is a graph of the temperature data obtained during an evaluation of the TLC electrode in an animal experiment. The TLC pad was constructed with '45-50° C.' TLC (R45C5W, B & H Liquid Crystal Resources, Riverside Buildings, Dock Road, Connah's Quay, Deeside, Flintshire, CH5 4DS, United Kingdom), which can be used to measure temperatures from 43° C. to 58° C. The pad has been applied in a 'near failure' state where only 10% of the pad is applied leading to very high temperatures occurring under the electrode.

The temperature was measured with a fluoroptic temperature probe, located between the electrode and the skin. Accurate monitoring equal to r=0.95±0.06 with the fluoroptic probes in the skin has been implemented. The temperature scale is given in seconds with the fluoroptic probe being measured every second and the TLC measured every 15 seconds. Note that the TLC does not report any temperature values when the tissue temperature is outside of its operating range of 43° C. to 58° C. The TLC layer can be used to give a quantitative measurement of temperature by interpreting the hue of the TLC at each point. This 'hue' value is easily read using a standard photographic image manipulation program such as Adobe Photoshop. The temperature has also been calculated for the TLC layer overlying the temperature probe. The temperature as measured by the probe and the TLC layer have a very high correlation (Pearson's correlation 0.98 where 1 is the highest possible correlation) indicating that the TLC layer can reliably measure the temperature at the return electrode.

TLC markings may be provided that indicate the state of the electrode below a predetermined temperature. The TLC markings may be visible below a temperature of about 31° C.; the TLC markings become clear at a temperature of 31° C. or above. The TLC markings may be used to indicate if the electrode is damaged or deteriorated. The TLC markings may indicate whether or not the electrode is adequately attached to tissue. The markings may comprise one or more symbols. Different TLC markings may be provided that indicate the state of the electrode above another predetermined temperature. The different TLC markings may indicate an abnormal condition of the electrode. The different TLC markings may be visible at or above a temperature of about 45° C. Another TLC layer may be provided having an irreversible temperature change property to permanently indicate when a predetermined temperature is exceeded. The other TLC layer may comprise one or more TLC stripes, which may be at least partially enclosed by an inert material such as polyurethane to prevent diffusion.

A photoconductive layer disposed between the TLC layer and the conductor may be provided, and ohmic connections coupled to the photoconductive layer may be provided that form an electrical connection if light is incident on the photoconductive layer. The photoconductive layer may be cadmium sulphide. An alarm may be triggered using the electrical connection. A threshold resistance may be set using a reference cell.

A contact with tissue may be formed using a conductive body, such as a jelly body, coupled to the electrode; or a capacitive coupling method may be used. A foam rubber peripheral body around the electrode and the conductive body may be provided.

The electrode may be viewed using a colour sensor and remotely observed using monitoring equipment coupled to the colour sensor.

Evaluation of a prototype TLC-equipped dispersive electrode pad (R45C5W, B & H Liquid Crystal Resources, Riverside Buildings, Dock Road, Connah's Quay, Deeside, Flintshire, CH5 4DS, United Kingdom) in an animal model shows a high correlation between the temperature measured using the TLC layer and fluoroptic temperature probes located between the electrode and the patient's skin. Thus, this indicates that the TLC-equipped dispersive electrode has high sensitivity and specificity for the presence of excessive heating.

The TLC-equipped dispersive electrode in accordance with the embodiments of the invention addresses the problem of burns associated with excessive heating at electrosurgical dispersive electrodes, which can be a serious complication of several surgical and percutaneous interventional procedures. The dispersive electrode with the TLC layer changes colour at sites of excessive heat and hence alerts an operator before a burn occurs. This electrode pad may be manufactured using relatively inexpensive materials and does not require specialised equipment to monitor the electrode pad. Optionally, the TLC-equipped electrode pad may be monitored using a video camera to make it even more convenient for the operator to assess the temperature at the return electrode.

In the foregoing manner, a number of dispersive electrode pads and methods of making and using such pads have been disclosed. The detailed description provides exemplary embodiments only and is not intended to limit the scope, applicability, or configuration of the invention. Rather, the detailed description of the exemplary embodiments provides those skilled in the art with enabling descriptions for implementing embodiments of the invention. It should be understood that various changes and/or substitutions may be made in the function and arrangement of elements without departing from the spirit and scope of the invention as set forth in the appended claims.

We claim:

1. A biomedical dispersive return electrode for electrosurgery or radiofrequency (RF) ablation, comprising:
   an electrode conductor that is a thin conductive layer adapted for receiving electrical energy from tissue via a return path; and
   a thermochromic liquid crystal (TLC) layer coupled to said electrode conductor, said TLC layer changing colour at one or more sites dependent upon the temperature of said conductor at each site, said TLC layer changing colour in a predetermined range of temperatures from about 40° C. to about 50° C. to alert an operator about the risk of a burn occurring.

2. The biomedical dispersive return electrode according to claim 1, wherein said electrical energy comprises electrical current delivered through a surgical instrument, or a catheter.

3. The biomedical dispersive return electrode according to claim 2, wherein said electrical current is delivered to tissue requiring treatment and said biomedical return electrode receives said electrical current via said return path.

4. The biomedical dispersive return electrode according to claim 1, wherein said electrode conductor comprises metal.

5. The biomedical dispersive return electrode according to claim 4, wherein said metal is aluminium.

6. The biomedical dispersive return electrode according to claim 1, wherein said electrode conductor is capacitively coupled with the tissue.

7. The biomedical dispersive return electrode according to claim 1, further comprising an electrical lead coupled to said electrode conductor for connection to an electrical device.

8. The biomedical dispersive return electrode according to claim 1, wherein said TLC layer is a single colour that changes colour at a predetermined temperature of 40° C.

9. The biomedical dispersive return electrode according to claim 1, further comprising TLC markings that indicate the state of the biomedical return electrode below a predetermined temperature.

10. The biomedical dispersive return electrode according to claim 9, wherein said TLC markings are visible below a temperature of about 31° C.

11. The biomedical dispersive return electrode according to claim 10, wherein said TLC markings become clear at a temperature of 31° C. or above.

12. The biomedical dispersive return electrode according to claim 9, wherein the absence of said TLC markings indicate to the user that the biomedical return electrode has been damaged or deteriorated.

13. The biomedical dispersive return electrode according to claim 9, wherein said TLC markings indicate whether or not said biomedical return electrode is adequately attached to tissue.

14. The biomedical dispersive return electrode according to claim 9, wherein said markings comprise one or more symbols.

15. The biomedical dispersive return electrode according to claim 1, wherein said TLC layer changes colour to one of a plurality of colours.

16. The biomedical dispersive return electrode according to claim 1, further comprising different TLC markings that indicate the state of said biomedical return electrode above another predetermined temperature.

17. The biomedical dispersive return electrode according to claim 16, wherein said different TLC markings are visible at or above a temperature of about 50° C.

18. The biomedical dispersive return electrode according to claim 1, further comprising a mylar backing upon which said TLC layer is formed.

19. The biomedical dispersive return electrode according to claim 1, further comprising another TLC layer having an irreversible temperature change property to permanently indicate when a predetermined temperature is exceeded.

20. The biomedical dispersive return electrode according to claim 19, wherein said other TLC layer comprises one or more TLC stripes.

21. The biomedical dispersive return electrode according to claim 20, wherein said one or more TLC stripes are at least partially enclosed by an inert material to prevent diffusion.

22. The biomedical dispersive return electrode according to claim 21, wherein said inert material comprises polyurethane.

23. The biomedical dispersive return electrode according to claim 1, further comprising:
a photoconductive layer disposed between said TLC layer and said electrode conductor; and
a plurality of ohmic connections coupled to said photoconductive layer that form an electrical connection if light is incident on said photoconductive layer.

24. The biomedical dispersive return electrode according to claim 23, where said TLC layer is formulated to be opaque at room temperature become clear above a specific temperature.

25. The biomedical dispersive return electrode according to claim 24, where said TLC layer is opaque at room temperature and becomes clear at 40° C.

26. The biomedical dispersive return electrode according to claim 23, wherein said photoconductive layer comprises cadmium sulphide.

27. The biomedical dispersive return electrode according to claim 23, wherein an alarm is triggered by said electrical connection.

28. The biomedical dispersive return electrode according to claim 23, further comprising a reference cell for setting a threshold resistance.

29. The biomedical dispersive return electrode according to claim 1, wherein a colour change of said TLC layer is a binary colour change at a predetermined temperature.

30. The biomedical dispersive return electrode according to claim 29, wherein the colour change of said TLC layer is irreversible.

31. The biomedical dispersive return electrode according to claim 1, wherein said TLC layer comprises a plurality of strips partially covering said electrode conductor.

32. The biomedical dispersive return electrode according to claim 1, wherein said TLC layer partially covers said electrode conductor.

33. A biomedical electrode pad, comprising:
at least one biomedical dispersive return electrode in accordance with claim 1; and
a conductive body coupled to said electrode to form a contact with tissue.

34. The biomedical electrode pad according to claim 33, wherein said conductive body is a jelly body.

35. The biomedical electrode pad according to claim 33, further comprising a foam rubber peripheral body around said electrode and said conductive body.

36. A system, comprising:
an apparatus for delivering electrical energy to tissue; and
a biomedical electrode pad in accordance with claim 33 coupled to said apparatus.

37. The system according to claim 36, further comprising:
a colour sensor for viewing said biomedical electrode pad; and
monitoring equipment coupled to said colour sensor for remotely observing said biomedical electrode pad.

38. The system according to claim 36, where said colour sensor is video camera.

39. A method of treating tissue using a biomedical dispersive return electrode for electrosurgery or radiofrequency (RF) ablation, said method comprising the steps of:
providing an electrode conductor that is a thin conductive layer adapted for receiving electrical energy from tissue via a return path; and
providing a thermochromic liquid crystal (TLC) layer coupled to said electrode conductor, said TLC layer changing colour at one or more sites dependent upon the temperature of said conductor at each site said TLC layer changing colour in a predetermined range of temperatures from about 40° C. to about 50° C. to alert an operator about the risk of a burn occurring.

40. The method according to claim 39, further comprising the step of delivering said electrical energy through a surgical instrument, or a catheter, said electrical energy comprising electrical current.

41. The method according to claim 40, wherein said electrical current is delivered to tissue requiring treatment and said electrode receives said electrical current via said return path.

42. The method according to claim 39, wherein said electrode conductor comprises metal.

43. The method according to claim 42, wherein said metal is aluminium.

44. The method according to claim 39, wherein said electrode conductor is capacitively couple with the tissue.

45. The method according to claim 39, further comprising the step of providing an electrical lead coupled to said electrode conductor for connection to an electrical device.

46. The method according to claim 39, wherein said TLC layer is a single colour that changes colour at a predetermined temperature of 40° C.

47. The method according to claim 39, further comprising the step of providing TLC markings that indicate the state of said biomedical dispersive return electrode below a predetermined temperature.

48. The method according to claim 47, wherein said TLC markings are visible below a temperature of about 31° C.

49. The method according to claim 48, wherein said TLC markings become clear at a temperature of 31° C. or above.

50. The method according to claim 48, wherein the absence of said TLC markings when said biomedical dispersive return electrode is examined at room temperature before application to the patient indicate that said biomedical dispersive return electrode is damaged or deteriorated.

51. The method according to claim 47, wherein the presence of said TLC markings when said biomedical dispersive return electrode is applied to the patient indicate that said biomedical dispersive return electrode is not adequately attached to tissue.

52. The method according to claim 47, wherein said markings comprise one or more symbols.

53. The method according to claim 39, wherein said TLC layer changes colour to one of a plurality of colours.

54. The method according to claim 39, further comprising the step of providing different TLC markings that indicate the state of the biomedical dispersive return electrode above another predetermined temperature.

55. The method according to claim 54, wherein said different TLC markings indicate an abnormal condition of said biomedical dispersive return electrode.

56. The method according to claim 55, wherein said different TLC markings are visible at or above a temperature of about 50° C.

57. The method according to claim 39, further comprising the step of providing a mylar backing upon which said TLC layer is formed.

58. The method according to claim 39, further comprising the step of providing another TLC layer having an irreversible temperature change property to permanently indicate when a predetermined temperature is exceeded.

59. The method according to claim 58, wherein said other TLC layer comprises one or more TLC stripes.

60. The method according to claim 59, wherein said one or more TLC stripes are at least partially enclosed by an inert material to prevent diffusion.

61. The method according to claim 60, wherein said an inert material comprises polyurethane.

62. The method according to claim 39, further comprising the steps of:
providing a photoconductive layer disposed between said TLC layer and said electrode conductor; and
providing a plurality of ohmic connections coupled to said photoconductive layer that form an electrical connection if light is incident on said photoconductive layer.

63. The method according to claim 62, wherein said TLC layer is formulated to be opaque at room temperature and become clear at a specified temperature.

64. The method according to claim 62, wherein said TLC layer is opaque at room temperature and becomes clear at 40° C.

65. The method according to claim 62, wherein said photoconductive layer comprises cadmium sulphide.

66. The method according to claim 62, further comprising the step of triggering an alarm using said electrical connection.

67. The method according to claim 62, further comprising the step of setting a threshold resistance using a reference cell.

68. The method according to claim 39, further comprising the step of forming a contact with tissue using a conductive body coupled to said biomedical dispersive return electrode.

69. The method according to claim 68, wherein said conductive body is a jelly body.

70. The method according to claim 68, further comprising the step of providing a foam rubber peripheral body around said biomedical dispersive return electrode and said conductive body.

71. The method according to claim 68, where said electrode conductor is capacitively coupled with said conductive body.

72. The method according to claim 68, further comprising the step of delivering electrical energy to tissue an apparatus for delivering such electrical energy.

73. The method according to claim 72, further comprising the steps of: viewing said biomedical dispersive return electrode using a colour sensor; and remotely observing said biomedical dispersive return electrode using monitoring equipment coupled to said colour sensor.

74. The method according to claim 73 where said colour sensor is a video camera.

75. The method according to claim 39, wherein a colour change of said TLC layer is a binary colour change at a predetermined temperature.

76. The method according to claim 75, wherein the colour change of said TLC layer is irreversible.

77. The method according to claim 39, wherein said TLC layer comprises a plurality of strips partially covering said electrode conductor.

78. The method according to claim 39, wherein said TLC layer partially covers said electrode conductor.

79. A biomedical dispersive return electrode for electrosurgery or radiofrequency (RF) ablation, comprising:
an electrode conductor that is a thin conductive layer adapted for conducting electrical energy; and
a thermochromic liquid crystal (TLC) layer coupled to said electrode conductor, at least a portion of said TLC producing a visible change that is binary in character if the temperature of said electrode conductor exceeds a predetermined temperature in the temperature range of about 40° C. to about 50° C. to indicate the risk of a burn.

80. The electrode according to claim 79, wherein said visible change comprises a binary colour change from a first colour to a second colour.

81. The electrode according to claim 79, wherein said visible change is irreversible.

82. The electrode according to claim 79, wherein said predetermined temperature is about 40° C.

83. The electrode according to claim 79, further comprising a mylar backing upon which said TLC layer is formed.

84. A method of providing a biomedical dispersive return electrode for electrosurgery or radiofrequency (RF) ablation, said method comprising the steps of:
- providing an electrode conductor that is a thin conductive layer adapted for conducting electrical energy; and
- providing a thermochromic liquid crystal (TLC) layer coupled to said electrode conductor, at least a portion of said TLC producing a visible change that is binary in character if the temperature of said electrode conductor exceeds a predetermined temperature in the temperature range of about 40° C. to about 50° C. to indicate the risk of a burn.

85. The method according to claim 84, wherein said visible change comprises a binary colour change from a first colour to a second colour.

86. The method according to claim 84, wherein said visible change is irreversible.

87. The method according to claim 84, wherein said predetermined temperature is about 40° C.

88. The method according to claim 84, wherein the electrode further comprises a mylar backing upon which said TLC layer is formed.

89. A biomedical dispersive return electrode for electrosurgery or radiofrequency (RF) ablation, comprising:
- an electrode conductor adapted for receiving electrical energy from tissue via a return path;
- a thermochromic liquid crystal (TLC) layer coupled to said electrode conductor, said TLC layer changing colour at one or more sites dependent upon the temperature of said conductor at each site, said TLC layer changing colour in a predetermined range of temperatures from about 40° C. to about 50° C. to alert an operator about the risk of a burn occurring;
- a photoconductive layer disposed between said TLC layer and said electrode conductor; and
- a plurality of ohmic connections coupled to said photoconductive layer that form an electrical connection if light is incident on said photoconductive layer.

90. A method of treating tissue using a biomedical dispersive return electrode for electrosurgery or radiofrequency (RF) ablation, said method comprising the steps of:
- providing an electrode conductor that is a thin conductive layer adapted for receiving electrical energy from tissue via a return path; and
- providing a thermochromic liquid crystal (TLC) layer coupled to said electrode conductor, said TLC layer changing colour at one or more sites dependent upon the temperature of said conductor at each site said TLC layer changing colour in a predetermined range of temperatures from about 40° C. to about 50° C. to alert an operator about the risk of a burn occurring;
- providing a photoconductive layer disposed between said TLC layer and said electrode conductor; and
- providing a plurality of ohmic connections coupled to said photoconductive layer that form an electrical connection if light is incident on said photoconductive layer.

* * * * *